US00PP17754P2

(12) United States Plant Patent
Hofmann

(10) Patent No.: US PP17,754 P2
(45) Date of Patent: May 22, 2007

(54) **NEW GUINEA *IMPATIENS* PLANT NAMED 'FISUPNIC PURPINK'**

(50) Latin Name: *Impatiens hawkeri*
Varietal Denomination: Fisupnic Purpink

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/330,817

(22) Filed: Jan. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new New Guinea *Impatiens* plant particularly distinguished by medium to large, round, cup-shaped, brilliant, rose-red to purple-pink flowers with white eyes, an early to medium flowering response, medium green foliage with short leaves, and a medium to tall plant habit that is round and bushy, is disclosed.

1 Drawing Sheet

Genus and species: *Impatiens hawkeri* W. Bull.
Variety denomination: 'Fisupnic Purpink'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisupnic Purpink'. The new cultivar originated from a hybridization made in the year 2002 in Hillscheid, Germany. The female parent was the proprietary New Guinea *Impatiens* plant 'K02-1236-1' (unpatented), while the male parent was the proprietary New Guinea *Impatiens* plant 'K02-374-1' (unpatented). The seeds produced by the hybridization were sown in a greenhouse in Portugal in the late Fall of 2002. A single plant selection was chosen for further evaluation and for asexual propagation in April 2003 in Moncarapacho, Portugal.

The new cultivar was created in 2002 in Hillscheid, Germany and has been asexually reproduced repeatedly by vegetative cuttings and tissue culture in Moncarapacho, Portugal and Hillscheid, Germany over a two-year period. 'Fisupnic Purpink' has not been observed under all possible environmental conditions. The present invention has been found to retain its distinctive characteristics through successive asexual propagations.

Plant Breeder's Rights for this cultivar were applied for in Switzerland on Mar. 30, 2005 and in Canada on Apr. 20, 2005.

SUMMARY OF THE INVENTION

The following are the most outstanding and distinguishing characteristics of this new cultivar when grown under normal horticultural practices in Hillscheid, Germany and Langley, British Columbia, Canada.

1. Brilliant, rose-red to purple pink flowers with white eyes;
2. Medium to large, round, cup-shaped flowers well above the foliage;

3. Uniform, medium green foliage with relatively short leaves;
4. A medium to tall size; round and bushy plant habit; and
5. An early to medium flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13-weeks old, grown in a greenhouse in Hillscheid, Germany, in late Spring.

DESCRIPTION OF THE NEW CULTIVAR

The following detailed descriptions set forth the distinctive characteristics of 'Fisupnic Purpink'. The data which define these characteristics were collected from asexual reproductions carried out in Hillscheid, Germany. The plant history was taken on 11- to 12-week old plants which were planted as rooted cuttings in 12-cm pots in late February 2005, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K02-1236-1' a proprietary purple-pink flowered New Guinea *Impatiens* plant (unpatented).

*Male parent.*—'K02-374-1' a proprietary light-pink flowered with magenta eyes New Guinea *Impatiens* plant (unpatented).

Growth:

*Growth and branching habit.*—Tall, round and bushy and well branched; the growth is indeterminate, though weak after the beginning of flowering.

*Height.*—15.0 cm.

*Width.*—25.5 cm.

*Propagation.*—Terminal tips for cuttings.

*Time to produce a finished flowering plant.*—9 to 10 weeks for a 12-cm pot.

*Time to initiate and develop roots.*—18 days at 22° C.

Branches:

*Average number.*—4.6.

*Length of branches.*—10 cm to 11 cm.

*Internode length.*—4.0 cm to 6.0 cm.

*Diameter of branches.*—0.6 cm to 0.7 cm.

*Stem color.*—RHS 146C (olive green) at midpoint to RHS 181A at the tips.

Leaves:

*Arrangement.*—Primarily in whorls.

*Size.*—Length: 11.2 cm. Width: 3.8 cm.

*Shape.*—Elliptic.

*Margin.*—Slightly serrate, ciliated.

*Apex.*—Acuminate.

*Base.*—Acute.

*Color* (*mature leaves*).—Upper surface: RHS 137B (medium-green). Lower surface: RHS 138B (light-green).

*Color* (*immature leaves*).—Upper surface: RHS 137B (medium-green). Lower surface: RHS 138B (light-green).

*Texture.*—Surface is somewhat slightly glossy, glabrous, smooth or somewhat rugose.

*Venation color.*—Upper surface: RHS 48A (reddish) mainly near the base. Lower surface: RHS N60A (dull purple).

*Variegation.*—None.

*Petioles.*—Length: 2.5 cm. Diameter: 0.3 cm to 0.4 cm. Color: Upper surface: RHS 53A. Lower surface: RHS N60A. Texture: Glabrous.

Flower buds:

*Shape.*—Ovoid.

*Size.*—Length: 2.3 cm. Diameter: 1.4 cm.

*Color.*—RHS N74A.

Inflorescence:

*Blooming habit.*—9 weeks after planting of rooted cuttings.

*Inflorescence type.*—Flowers appear solitary in the leaf axils of the upper nodes of the stems.

*Number of flowers per node.*—7 to 9, in various stages of development.

*Flowering season.*—Indeterminate, continuously from March to October, depending on light intensity.

*Lastingness of individual blooms.*—Up to 14 days (in a greenhouse in the Spring at 18° C.).

*Peduncle.*—Color: RHS 184A (dull purple). Size: Length: 5.0 cm to 5.5 cm. Diameter: 0.15 cm. Texture: Glabrous, flexible.

Flowers:

*Form of corolla.*—Single-type, 5 petals.

*Shape of corolla.*—Nearly round, with the petals overlapping, slightly cup-shaped. shaped.

*Corolla size.*—Length: 7.2 cm. Width: 6.9 cm. Depth: 1.2 cm.

Petals:

*Shape.*—Cordate, shallow lobes at the top end, top petal slightly cupped.

*Apex.*—Retuse.

*Base.*—Attenuate.

*Margin.*—Entire.

*Petal size.*—Top: Length: 2.9 cm. Width: 5.4 cm. Lateral: Length: 3.3 cm. Width: 4.3 cm. Lower: Length: 3.3 cm. Width: 4.8 cm.

*Color.*—General color description: Deep purple-pink to rose-red, white at the base. Upper surface: RHS N57B, later between RHS N57B and RHS N57C, no markings; RHS 69B to RHS 155D (pale pink to white) near the bases. Lower surface: From RHS 58B to RHS 58C. Eye Zone: RHS N66B (red-purple), small.

*Petal texture.*—Smooth.

*Aspect.*—Flat to slightly cupped.

Spur:

*Shape.*—Downwardly curved.

*Color.*—RHS 53B (red-purple) at tip, to RHS 53D (at the flower end).

*Size.*—Length: 5.0 cm to 6.0 cm. Diameter: 0.3 cm (at the flower end).

Reproductive organs:

*Stamens.*—Number: 5 fused. Stamen color (upper surface color): RHS N66C. Anthers: Fused, hooded. Pollen color: RHS 8D (whitish-yellow).

*Pistils.*—Style and stigma: 5, very short, RHS 150D (pale-yellow). Ovary: 5-celled. Ovary length: 0.5 cm. Ovary color: Initially RHS 137D (light-green) becoming RHS 139A (darker green).

Fruit and seed set: No seed set observed.

Disease and insect resistance: No particular resistance or susceptibility has been observed.

COMPARISON WITH PARENTAL AND COMMERCIAL CULTIVARS

'Fisupnic Purpink' differs from the female parent 'K02-1236-1' (unpatented) by having a somewhat less deep overall flower color and an earlier flowering response than 'K02-1236-1'.

'Fisupnic Purpink' differs from the male parent 'K02-374-1' (unpatented), by having a light-pink to rose-red/purple-pink flower color, while 'K02-374-1' has light pink flowers with magenta eyes. Additionally, 'Fisupnic Purpink' has a somewhat tighter plant habit than 'K02-374-1'.

'Fisupnic Purpink' differs from the commercial cultivar 'Fisupnic Hotpink' (U.S. Plant Patent Applied for) by having larger flowers of a less bluish hue, with a distinct eye and flatter, less often cup-shaped flowers, and a less vigorous growth habit than 'Fisupnic Hotpink'.

'Fisupnic Purpink' differs from cultivar 'Fisnics Hot Pink' (U.S. Plant Pat. No. 14,811) by having less bluish, more reddish hue of flower color than 'Fisnics Hot Pink'. Additionally, 'Fisupnic Purpink' has medium green, while 'Fisnics Hot Pink' has dark-green foliage.

I claim:

1. A new and distinct cultivar of New Guinea *Impatiens* plant as shown and described herein.

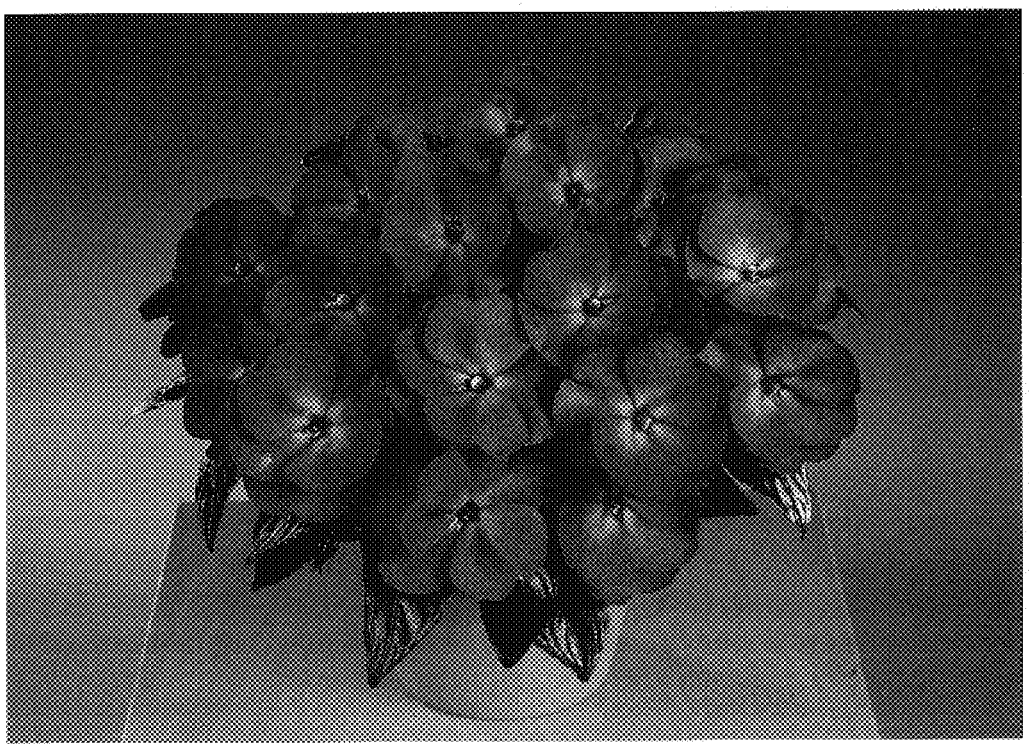

* * * * *